United States Patent [19]

Kayou et al.

[11] Patent Number: 6,166,241

[45] Date of Patent: Dec. 26, 2000

[54] PROCESS FOR THE SIMULTANEOUS PREPARATION OF ACRYLONITRILE AND ARCYLIC ACID

[75] Inventors: Atsushi Kayou; Tatsuya Ihara, both of Okayama, Japan

[73] Assignee: Mitsubishi Chemical Corporation, Tokyo, Japan

[21] Appl. No.: 09/284,993

[22] PCT Filed: Nov. 17, 1997

[86] PCT No.: PCT/JP97/04169

§ 371 Date: May 13, 1999

§ 102(e) Date: May 13, 1999

[87] PCT Pub. No.: WO98/22421

PCT Pub. Date: May 28, 1998

[30] Foreign Application Priority Data

Nov. 15, 1996 [JP] Japan ................................. 8-304502

[51] Int. Cl.$^7$ ............................ C07C 253/00; C07C 51/16

[52] U.S. Cl. ............................................. 558/318; 562/549

[58] Field of Search ............................. 558/318; 562/549

[56] References Cited

U.S. PATENT DOCUMENTS 5,380,933   1/1995   Ushikubo et al. ..................... 562/549

*Primary Examiner*—Cecilia Tsang
*Assistant Examiner*—Joseph Murray
*Attorney, Agent, or Firm*—Oblon, Spivak, McClelland, Maier & Neustadt, P.C.

[57] ABSTRACT

The present invention relates to a method for the simultaneous production of acrylonitrile and acrylic acid by reacting propane with ammonia and oxygen in the gas phase catalytic oxidation in the presence of a metal oxide catalyst containing vanadium and at least one member selected from tellurium, antimony and molybdenum and adjusting the molar ratio of propane to ammonia to from 2 to 10 and the molar ratio of oxygen to ammonia to from 2 to 10.

13 Claims, 2 Drawing Sheets

PROCESS FOR THE SIMULTANEOUS PREPARATION OF ACRYLONITRILE AND ARCYLIC ACID

This application is a 371 of PCT/JP97/04169 filed Nov. 17, 1997.

TECHNICAL FIELD

The present invention relates to a method for simultaneous production of acrylonitrile and acrylic acid. Particularly, the present invention relates to a method for simultaneously producing acrylonitrile and acrylic acid by reacting propane with ammonia and oxygen under specific catalyst and operation conditions, which is a method for producing constantly over a long period of time.

BACKGROUND ART

Acrylonitrile is industrially important as a material for synthetic resins, synthetic fibers, synthetic rubbers, etc., while acrylic acid is also industrially important as a material for highly water absorptive resins, synthetic resins, coating materials, adhesives, plasticizers, etc. Heretofore, acrylonitrile has been produced by reacting propylene with ammonia for gas phase catalytic oxidation, while acrylic acid has been produced by a two step gas phase catalytic oxidation reaction of propylene. Recently, an attention has been drawn to a method for production of an unsaturated nitrile wherein a more inexpensive alkane is used as a starting material. Particularly, from the difference in price between propylene and propane, an attention has been drawn to a method for production of acrylonitrile or acrylic acid wherein inexpensive propane is used as a starting material, and proposals for a catalyst and a process have been made. Among them, an interest has been drawn to development of a method for production of acrylonitrile by a so-called ammoxidation reaction method wherein propane is used as a starting material and reacted with ammonia and oxygen in a gas phase for catalytic oxidation in the presence of a catalyst.

With respect to the method for production of acrylonitrile by this ammoxidation of propane, methods have been proposed wherein as the catalyst, for example, a Mo—Bi—P type catalyst (JP-A-48-16887), a Mo—Cr—Te type catalyst (U.S. Pat. No. 5,171,876), a V—Sb type catalyst (JP-A-47-33783, JP-B-50-23016, JP-A-1-268668, JP-A-2-180637), a V—Sb—U—Ni type catalyst (JP-B-47-141371), or a V—Sb—W—P type catalyst (JP-A-2-95439) is used. Further, recently, a Mo—V—Te type catalyst (JP-A-2-257, JP-A-5-148212, JP-A-5-208136, JP-A-6-279351, JP-A-6-287146, JP-A-7-108101), or a Mo—V—Sb type catalyst (JP-A-9-157241), has been proposed as an effective catalyst.

Further, JP-A-3-27350 proposes a method wherein unreacted propane is separated and recovered from a gas discharged from a reactor and again used as a starting material gas for reaction, thereby increasing the yield of acrylonitrile from propane.

On the other hand, also in a method for production of an unsaturated carboxylic acid, an attention has been drawn to a method wherein a more inexpensive alkane is used as a starting material. Particularly, with respect to production of acrylic acid in one step by a gas phase catalytic oxidation reaction method wherein inexpensive propane is used as a starting material and subjected to catalytic oxidation with oxygen in a gas phase in the presence of a catalyst, a method has been proposed in which as a catalyst, a Bi—Mo—V type and/or divanadyl pyrophosphate catalyst (JP-A-3-170445, the 11th International Catalyst Meeting, Collection of Summaries, p.1205-1214) or a P—Mo—Sb—W type catalyst (Belgian Patent Application No. 9500449) is used. However, recently, it has been proposed that a Mo—V—Te type catalyst (JP-A-6-279351) can be used.

However, the above-mentioned production methods heretofore proposed, are directed to produce them separately by totally independent reaction apparatus, and not intended to produce both of them simultaneously. Of course, nothing is disclosed with respect to the reaction operation conditions for producing both.

DISCLOSURE OF INVENTION

The present inventors have found that among the above catalysts, some catalysts have an ability to simultaneously produce both of acrylonitrile and acrylic acid under specific ammoxidation conditions. If both of acrylonitrile and acrylic acid can simultaneously be produced, investment to installation of the reaction apparatus can be reduced to a large extent, and yet if the selectivity and yield in the total amount of acrylonitrile and acrylic acid, can be increased, such will be advantageous from the changeable cost of the starting material. Further, a method has been found whereby decrease with time of the catalyst performance can be suppressed, and the catalyst performance is constant over a long period of time, whereby an industrially extremely effective method has been found for the method for simultaneous production of acrylonitrile and acrylic acid, which has heretofore not been considered.

Namely, the present inventors have found it possible to produce acrylonitrile and acrylic acid simultaneously by reacting propane with ammonia under specific catalyst and specific operation conditions and to optionally control the ratio of formation of acrylonitrile and acrylic acid. Further, by adopting such a simultaneous production method, the selectivity and yield in the total amount of acrylonitrile and acrylic acid can be increased, and a method for improving the stability with time of the catalytic performance, can be presented.

Namely, the gist of the present invention resides in, in a method for producing acrylonitrile or acrylic acid by reacting propane with ammonia and oxygen for gas phase catalytic oxidation in the presence of a metal oxide catalyst containing vanadium and at least one member selected from tellurium, antimony and molybdenum, a method for simultaneous production of acrylonitrile and acrylic acid, characterized by simultaneously producing acrylonitrile and acrylic acid by adjusting the molar ratio of propane to ammonia to from 2 to 10 and the molar ratio of oxygen to ammonia to from 2 to 10.

Here, "simultaneously producing" means "producing together" and is meant for "both will be produced".

BEST MODE FOR CARRYING OUT THE INVENTION

Figure 1:
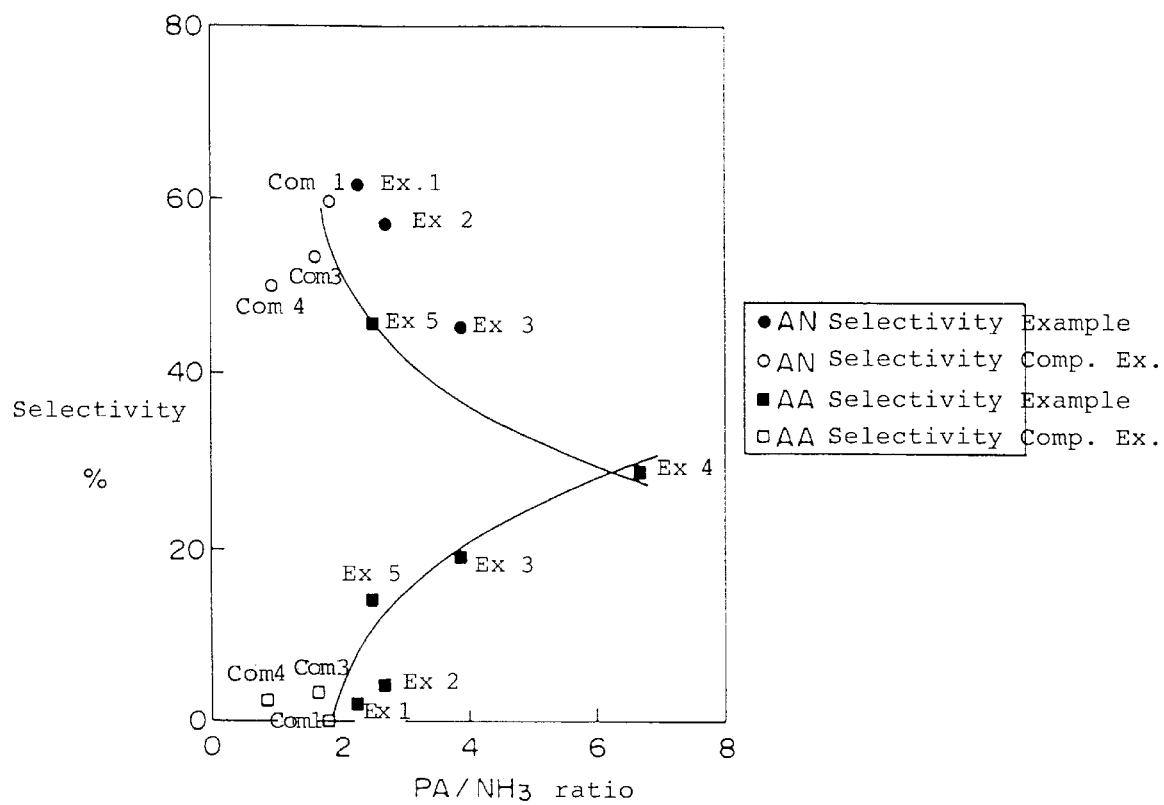
FIG. 1 shows the relation between the PA (propane)/$NH_3$ ratio and the selectivity for acrylonitrile (AN) and the selectivity for acrylic acid (AA), in the method of the present invention.
Figure 2:
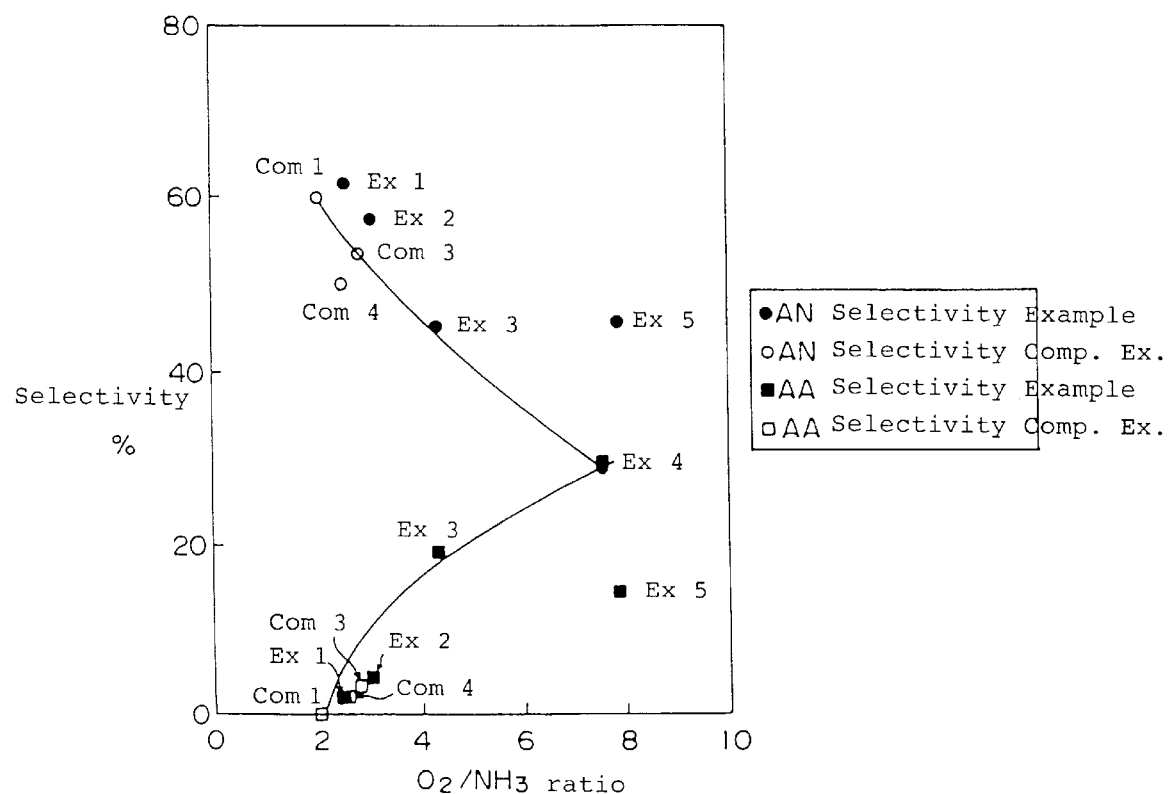
FIG. 2 shows the relation between the $O_2$/$NH_3$ ratio and the selectivity for AN and the selectivity for AA, in the method of the present invention.

Now, the present invention will be described in detail.

In the present invention, propane, ammonia and oxygen are reacted for catalytic oxidation in the presence of a specific composite metal oxide.

The composite metal oxide catalyst is one containing vanadium, and at least one member selected from tellurium, antimony and molybdenum, as essential components. Among them, one containing molybdenum and vanadium as essential components, or one containing tellurium and/or antimony as an essential component, is preferred. More preferred may be a composite metal oxide catalyst which contains molybdenum, vanadium, X, Y and oxygen (wherein X is at least one member among tellurium and antimony, and Y is at least one element selected from the group consisting of niobium, tantalum, tungsten, titanium, aluminum, zirconium, chromium, manganese, iron, ruthenium, cobalt, rhodium, nickel, palladium, platinum, bismuth, boron, indium, phosphorus, a rare earth element, an alkali metal and an alkaline earth metal), as essential components, and the proportions of the above respective essential components except for oxygen, are represented by the following formulae:

$$0.25 < rMo < 0.98$$

$$0.003 < rV < 0.5$$

$$0.003 < rX < 0.5$$

$$0.003 < rY < 0.5$$

(wherein rMo, rV, rX and rY represent the molar fractions of Mo, V, X and Y, based on the total of the above essential components except for oxygen).

Other than essential components of molybdenum, vanadium, and tellurium and/or antimony, at least one element among niobium, tungsten, titanium, tantalum, boron and cerium, is preferably contained as an optional component, and among them, niobium is particularly preferred, and more preferably, in addition to niobium, boron and/or cerium is contained.

As specific examples of the composite metal oxide catalyst to be used in the present invention, catalysts of the following 1) to 6) may, for example, be mentioned.

1) Mo—V—Nb—Te—O type catalyst (see JP-A-2-257)

$$Mo_{1.0}V_aTe_bNb_cO_x$$

(In the above formula, a, b and c represent atomic ratios of the respective constituting elements relative to one atom of Mo, wherein a=0.01 to 1.0, b=0.1 to 0.5, and c=0.01 to 1.0, and x is a number determined by the valencies of metal elements.)

2) Mo—V—Te—Nb—X—O type catalyst (see JP-A-5-148212)

$$Mo_aV_bTe_cNb_dX_xO_n$$

(In the formula, X is one or more elements selected among Mg, Ca, Sr, Ba, Al, Ga, Tl, In, Ti, Zr, Hf, Ta, Cr, Mn, W, Fe, Ru, Co, Rh, Ni, Pd, Pt, Zn, Sn, Pb, As, Sb, Bi, La and Ce; when a=1, b=0.01 to 1.0, c=0.01 to 1.0, d=0 to 1.0, and x=0.0005 to 1.0, and n is a number determined by the oxidized states of other elements.)

3) Mo—V—Te—X—O type catalyst (see JP-A-5-208136, JP-A-5-279313)

$$Mo_aV_bTe_cX_xO_n—Z_zO_m$$

(In the formula, X is one or more elements selected among Nb, Ta, W, Ti, Al, Zr, Cr, Mn, Fe, Ru, Co, Rh, Ni, Pd, Pt, Sb, Bi and Ce, and Z is at least one element selected among Sb, Bi, Ce and B, and when a=1, b=0.01 to 1.0, c=0.01 to 1.0, x=0.01 to 1.0, and z=0 to 1.0, and n and m are determined by the oxidized states of other elements.)

4) X—Cr—Mo—Bi—Y—O type catalyst (see JP-A-6-116225)

$$X_aCr_bMo_cBi_dY_eO_n$$

(In the formula, X is Nb and/or Ta, Y is one or more elements selected among Te, In, W, Ti, Al, Zr, Mn, Fe, Ru, Co, Rh, Ni, Pd, Pt, Sb, Bi and Ce, when a=10, b=0.5 to 5, c=0.2 to 5, d=0.2 to 5, and e=0 to 5, and n is determined by the oxidized states of other elements.)

5) Mo—Cr—Bi—X—O type catalyst (see JP-A-7-215925)

$$Mo_aCr_bBi_cX_dO_n$$

(In the formula, X is at least one member selected among an alkali metal, an alkaline earth metal, Al, Zr, Ni, Co, Ce, Nb, Ta, W, Ti, Mn, Ru, Rh, Pd, Pt, Sb, B, In, La, P, Sn, Pb and Cu, when a=1, b=0.01 to 10, c=0.01 to 10, and d=0 to 100, and n is determined by the oxidized states of other elements.)

6) V—Sb type catalyst (see JP-A-1-268668, JP-A-2-180637)

This is a composite oxide catalyst which contains V and Sb as essential components and may further contain W, P, Sn, etc., as optional components.

Among these, 1) a Mo—V—Nb—Te—O type catalyst, 2) Mo—V—Te—Nb—X—O type catalyst and 3) Mo—V—Te—X—O type catalyst are preferred, since acrylonitrile and acrylic acid can thereby be obtained at high selectivity at a relatively low temperature of from 340° C. to 480° C.

The production methods and the starting materials for the above composite metal oxide catalysts are not particularly limited, but a method is commonly employed wherein a solution or slurry of water or an organic solvent containing component elements of the starting materials, is prepared, then dried and calcined.

For example, as a method for production of a composite metal oxide containing molybdenum, vanadium, tellurium and niobium, an aqueous solution of telluric acid, an aqueous solution of ammonium niobium oxalate and an aqueous solution of ammonium paramolybdate are sequentially added to an aqueous solution of ammonium metavanadate in such a ratio that the atomic ratio of the respective metal elements will be the predetermined proportions, followed by drying by e.g. an evaporation to dryness method, a spray drying method, a freeze drying method or a vacuum drying method, to obtain a dried product, and then the obtained dried product is calcined to obtain the composite metal oxide.

Such a composite metal oxide catalyst may be used alone, but a well known carrier component such as silica, alumina, titania, zirconia, aluminosilicate or diatomaceous earth, may, for example, be used. Otherwise, the catalyst component may be diluted with such a material, so that it is used as a mixture containing the catalyst component in an amount of from 1 to 90 wt %.

Further, the catalyst may be formed into a suitable shape and particle size depending upon the scale and the system of the reaction.

Using the complex metal oxide catalyst thus produced, the operation conditions for the catalytic oxidation reaction of propane, ammonia and oxygen are set to be the conditions proposed by the present invention, whereby acrylonitrile and acrylic acid can be formed at high selectivity in the total amount, and the catalyst can be maintained at a high selectivity of at least 60% in the total amount of acrylonitrile and acrylic acid over a long period of time of at least 7000 hours, and thus the reaction can be carried out constantly over a long period of time. As such reaction operation condition, it is necessary to adjust the molar ratio of propane to ammonia to from 2 to 10, preferably from 2.5 to 10, and the molar ratio of oxygen to ammonia to from 2 to 10, preferably from 3 to 8.

Further, when the molar ratio of formed acrylonitrile and acrylic acid is from 0.01 to 5.0, preferably from 0.05 to 2.0, the yield and the selectivity in the total amount of acrylonitrile and acrylic acid, will increase. Further, when such reaction operation conditions and the proportions of formed acrylonitrile and acrylic acid are set, decrease with time of the catalytic performance will be suppressed, and the catalytic performance can be maintained constantly over a long period of time.

The propane to be used in the present invention may be one having an industrial purity and may contain a small amount of a gas which will not be influential to the reaction, such as methane, ethane, butanes, propylene, carbon monoxide or carbon dioxide, without any trouble. Further, the ammonia may be one having an industrial purity, and may be diluted with other gas which will not adversely affect the reaction.

The oxygen may be pure oxygen gas. However, purity is not particularly required, and it is usually economical to use an oxygen-containing gas such as air.

The reaction gas to be supplied may contain, in addition to the gas components for such a reaction, a small amount of a gas inert to the reaction, such as nitrogen, argon, steam, carbon dioxide or helium, without any trouble so long as formation of acrylonitrile or acrylic acid is concerned.

The reactor may be of any system such as a fixed bed or fluidized bed system. However, since the reaction is an exothermic reaction, a fluidized bed system is preferred as the control of the reaction temperature is easy.

This reaction is usually carried out under atmospheric pressure, but it may be carried out under low pressure or reduced pressure. Further, the gas space velocity SV in the gas phase catalytic reaction is usually within a range of from 100 to 10000/h, preferably from 500 to 9000/h. Further, the space velocity WHSV based on mass of propane is within a range of from 0.05 to 6.0/h, preferably from 0.07 to 4.0/h, and the space velocity WHSV based on mass of oxygen is usually within a range of from 0.05 to 6.0/h, preferably from 0.2 to 4.5/h. The reaction temperature is usually within a range of from 340 to 480° C., preferably from 380 to 460°C.

Depending upon the reaction operation conditions, unreacted propane may be discharged in a substantial amount from the reactor. Such unreacted propane and propylene formed in a small amount may be recovered by a method as disclosed in JP-A-3-27350 and may be supplied again to the reactor for reuse, such being economical.

Further, by the method of the present invention, in addition to acrylonitrile and acrylic acid, carbon monoxide, carbon dioxide, acetonitrile, prussic acid, acrolein, acetic acid, etc., may be formed as byproducts, but their amount is sufficiently small as compared with acrylonitrile and acrylic acid.

The formed gas containing acrylonitrile and acrylic acid, discharged from the reactor, is absorbed in a dilute sulfuric acid aqueous solution to remove unreacted ammonia in the same manner as in the system for producing acrylonitrile from propylene, and then separated by distillation operation to an aqueous solution containing acrylonitrile and acrylic acid. From the obtained aqueous solution, acrylonitrile and acrylic acid may be separated by a method such as distillation and can be used for the respective uses. Further, by adopting the method proposed by the present invention, the efficiency for utilizing ammonia for acrylonitrile can be increased, and in other words, the amount of unreacted ammonia can be reduced, whereby treatment with dilute sulfuric acid, and treatment of the resulting ammonium sulfate can be reduced. Further, by the method of the present invention, in addition to acrylonitrile and acrylic acid, carbon monoxide, carbon dioxide, acetonitrile, prussic acid, acrolein, acetic acid, etc. may be formed as byproducts, but their amount is small.

In the production in an industrial scale, unreacted propane may be incinerated, but the off-gas after the reaction contains a useful product such as propylene, and it is more economical to recover and reuse unreacted propane and propylene.

EXAMPLES

Now, the present invention will be described in detail with reference to Examples and Reference Examples. However, the present invention is by no means restricted to these Examples unless it exceeds the gist thereof.

The analyses of the reaction products were carried out by gas chromatography.

Further, the conversion (%) and the selectivity (%) in the following Examples and Comparative Examples are, respectively, represented by the following formulae.

Propane conversion (%)=(mols of consumed propane/mols of supplied propane)×100

Acrylonitrile selectivity (%)=(mols of formed acrylonitrile/mols of consumed propane)×100

Acrylic acid selectivity (%)=(mols of formed acrylic acid/mols of consumed propane)×100

Propylene selectivity (%)=(mols of formed propylene/mols of consumed propane)×100

CATALYST PRODUCTION EXAMPLE 1

An oxide catalyst having an empirical formula of $Mo_{1.0}V_{0.3}Nb_{0.12}Te_{0.23}O_n$ was prepared by a method disclosed in Example 1 of JP-A-5-279313, as shown below.

15.7 g of ammonium metavanadate was dissolved in 325 ml of warm water, and 23.6 of telluric acid and 78.9 g of a para-molybdate were sequentially added thereto to prepare a uniform aqueous solution. Further, 117.5 g of an aqueous ammonia niobium oxalate solution having a niobium content of 0.456 mol/kg, was mixed thereto to prepare a slurry. This slurry was evaporated to dryness to obtain a solid. This solid was molded and pulverized, and then calcined in a nitrogen stream at 600° C. for 2 hours.

CATALYST PRODUCTION EXAMPLE 2

An oxide catalyst having an empirical formula of $MO_{1.0}V_{0.3}Nb_{0.12}Te_{0.23}Co_{0.05}O_n$ was prepared by the following method.

15.7 g of ammonium metavanadate was dissolved in 325 ml of warm water, and 23.6 g of telluric acid, 78.9 g of a para-molybdate and 2.23 g of cobalt acetate were sequentially added thereto to prepare a uniform aqueous solution. Further, 117.5 g of an aqueous ammonia niobium oxalate solution having a niobium concentration of 0.456 mol/kg, was mixed thereto to prepare a slurry. This slurry was evaporated to dryness to obtain a solid. This solid was molded and pulverized, and then calcined in a nitrogen stream at 600° C. for 2 hours.

EXAMPLE 1

600 g of the oxide of Catalyst Production Example 1 was packed into a 2 inch fluidized bed reactor, and a 3800 hr gas phase oxidation reaction was carried out at a reaction temperature of 465° C. by supplying a gas of propane:ammonia:air=1:1.2:19 mol ratio at a space velocity WHSV based on mass of propane=0.165/h. 0.1 g of the catalyst subjected to this 3800 hr reaction, was packed into a fixed bed reactor made of glass having a diameter of 6 mm, and a gas phase oxidation reaction was carried out at a reaction temperature of 434° C. by supplying a gas of propane:ammonia:air=1:0.44:5.40 molar ratio at a space velocity WHSV based on mass of propane=2.53/h, a space velocity WHSV based on mass of oxygen=2.08/h and a gas space velocity SV=8713/h. The results are shown in Table 1 given hereinafter.

EXAMPLE 2

0.1 g of the catalyst used for the same 3800 hr reaction as in Example 1, was packed into the reactor in the same manner as in Example 1, and a gas phase oxidation reaction was carried out at a reaction temperature of 433° C. by supplying a gas of propane:ammonia:air=1:0.37:5.40 molar ratio at a space velocity WHSV based on mass of propane=2.53/h. The results are shown in Table 1 given hereinafter.

EXAMPLE 3

0.1 g of the catalyst used in the same 3800 hr reaction as in Example 1, was packed into the reactor in the same manner as in Example 1, and a gas phase oxidation reaction was carried out at a reaction temperature of 434° C. by supplying a gas of propane:ammonia:air=1:0.26:5.40 molar ratio at a space velocity WHSV based on mass of propane=2.53/h. The results are shown in Table 1 given hereinafter.

EXAMPLE 4

0.1 g of the catalyst used in the same 3800 hr reaction as in Example 1, was packed into the reactor in the same manner as in Example 1, and a gas phase oxidation reaction was carried out at a reaction temperature of 431° C. by supplying a gas of propane:ammonia:air=1:0.15:5.40 molar ratio at a space velocity WHSV based on mass of propane=2.53/h. The results are shown in Table 1 given hereinafter.

COMPARATIVE EXAMPLE 1

(a case where no acrylic acid was formed)

0.1 g of the catalyst used in the same 3800 hr reaction as in Example 1, was packed into the reactor in the same manner as in Example 1, and a gas phase oxidation reaction was carried out at a reaction temperature of 433° C. by supplying a gas of propane:ammonia:air=1:0.55:5.40 molar ratio at a space velocity WHSV based on mass of propane=2.53/h. The results are shown in Table 1 given hereinafter.

COMPARATIVE EXAMPLE 2

(a case where no acrylonitrile was formed)

0.1 g of the catalyst used in the same 3800 hr reaction as in Example 1, was packed into the reactor in the same manner as in Example 1, and a gas phase oxidation reaction was carried out at a reaction temperature of 433° C. by supplying a gas of propane:air=1:5.40 molar ratio at a space velocity WHSV based on mass of propane=2.53/h. The results are shown in Table 1 given hereinafter.

EXAMPLE 5

0.55 g of the catalyst used in the same 3800 hr reaction as in Example 1, was packed into the reactor in the same manner as in Example 1, and a gas phase oxidation reaction was carried out at a reaction temperature of 378° C. by supplying a gas of propane:ammonia:air=1:0.40:15.0 molar ratio at a space velocity WHSV based on mass of propane=0.109/h. The results are shown in Table 1 given hereinafter.

COMPARATIVE EXAMPLE 3

0.6 g of the catalyst used in the same 3800 hr reaction as in Example 1, was packed into the reactor in the same manner as in Example 1, and a gas phase oxidation reaction was carried out at a reaction temperature of 404° C. by supplying a gas of propane:ammonia:air=1:0.60:8.00 molar ratio at a space velocity WHSV based on mass of propane=2.73/h. The results are shown in Table 1 given hereinafter.

COMPARATIVE EXAMPLE 4

0.55 g of the oxide of Catalyst Production Example 2 was packed into the reactor in the same manner as in Example 1, and a gas phase oxidation reaction was carried out at a reaction temperature of 447° C. by supplying a gas of propane:ammonia:air=1:1.20:15.0 molar ratio at a space velocity WHSV based on mass of propane=0.182/h. The results are shown in Table 1 given hereinafter.

TABLE 1

| | Temp. ° C. | WHSV 1/h | Propane molar ratio | $NH_3$ molar ratio | Air molar ratio | Propane conversion % | Acrylonitrile selectivity %*1 | Acrylic acid selectivity %*2 | Propylene selectivity %*3 | Total of *1 + *2 + *3 % | PA/$NH_3$ | $O_2$/$NH_3$ |
|---|---|---|---|---|---|---|---|---|---|---|---|---|
| Ex. 1 | 434 | 2.53 | 1.0 | 0.44 | 5.40 | 24.5 | 61.6 | 2.0 | 15.9 | 79.5 | 2.27 | 2.57 |
| Ex. 2 | 433 | 2.53 | 1.0 | 0.37 | 5.40 | 25.3 | 57.3 | 4.2 | 15.4 | 76.9 | 2.70 | 3.05 |
| Ex. 3 | 434 | 2.53 | 1.0 | 0.26 | 5.40 | 25.6 | 45.3 | 19.1 | 14.8 | 79.2 | 3.85 | 4.35 |
| Ex. 4 | 431 | 2.53 | 1.0 | 0.15 | 5.40 | 23.3 | 28.8 | 29.4 | 16.3 | 74.5 | 6.67 | 7.53 |
| Ex. 5 | 378 | 0.109 | 1.0 | 0.4 | 15.0 | 52.4 | 45.8 | 14.4 | 4.2 | 64.4 | 2.5 | 7.85 |
| Comp. Ex. 1 | 433 | 2.53 | 1.0 | 0.55 | 5.40 | 22.4 | 59.8 | 0.00 | 17.9 | 77.7 | 1.8 | 2.05 |
| Comp. Ex. 2 | 431 | 2.53 | 1.0 | 0.00 | 5.40 | 18.2 | 0.00 | 35.5 | 20.9 | 56.4 | ∞ | ∞ |
| Comp. Ex. 3 | 404 | 2.73 | 1.0 | 0.60 | 8.00 | 54.6 | 53.4 | 3.3 | 4.0 | 60.7 | 1.67 | 2.8 |
| Comp. Ex. 4 | 447 | 0.182 | 1.0 | 1.2 | 15.0 | 91.4 | 50.9 | 2.30 | 0.0 | 53.2 | 0.83 | 2.62 |

EXAMPLE A (Catalyst life test)

The oxide catalyst produced in Catalyst Production Example 1 was packed into the reactor, and a gas phase oxidation reaction was carried out at a reaction temperature of 430° C. by supplying a gas having the same reaction gas composition as in Example 2 (propane:ammonia:air= 1:0.37:5.40 molar ratio) at the same space velocity WHSV based on mass of propane=2.53/h, a space velocity WHSV based on mass of oxygen=1.68/h and a gas space velocity of 8713/h. The results after 0 hour of this reaction, and the results after 7175 hours are shown in Table 2 given hereinafter.

COMPARATIVE EXAMPLE B (Catalyst life test)

The oxide catalyst produced in Catalyst Production Example 1 was packed into the reactor, and a gas phase oxidation reaction was carried out at a reaction temperature of 440° C. by supplying a gas having the same reaction gas composition as in Comparative Example 3 (propane:ammonia:air=1:0.6:8.00 molar ratio) at a same space velocity WHSV based on mass of propane=1.375/h, a space velocity WHSV based on mass of oxygen=1.68/h and a gas space velocity of 6720/h. The results after 0 hour of this reaction, and the results after 4804 hours, are shown in Table 2 given hereinafter.

COMPARATIVE EXAMPLE C (Catalyst life test)

The oxide catalyst produced in Catalyst Production Example 1 was packed into the reactor, and a gas phase oxidation reaction was carried out at a reaction temperature of 430° C. by supplying a gas having the same reaction gas composition as in Comparative Example 4 (propane:ammonia:air=1:1.2:15.0 molar ratio) at the same space velocity WHSV based on mass of propane=0.182/h, a space velocity WHSV based on mass of oxygen=0.42/h and a gas space velocity of 1594/h. The results after 0 hour of this reaction and the results after 3524 hours are shown in Table 2 given hereinafter.

TABLE 2

| | | Catalyst life tests | | | | |
|---|---|---|---|---|---|---|
| | | Propane conversion | Acrylonitrile selectivity | Acrylic acid selectivity | Propylene selectivity | Total selectivity % |
| Example A | Reaction time (h) 0 | 33.8 | 54.8 | 14.88 | 10.65 | 80.33 |
| | Reaction time (h) 7175 | 17.1 | 46.4 | 5.26 | 23.04 | 74.70 |
| | Decrease in selectivity | | −8.4 | −9.62 | 12.39 | −5.63 |
| | Decreasing rate of selectivity (%/h) | | −0.001171 | −0.001341 | 0.0017268 | −0.000784 |
| | Decrease in selectivity per propane WHSV (% h) | | −3.322785 | −3.804786 | 4.9011266 | −2.226444 |
| Comparative Example B | Reaction time (h) 0 | 46.3 | 61.6 | 2.38 | 7.13 | 71.10 |
| | Reaction time (h) 4804 | 42.1 | 48.4 | 2.07 | 2.61 | 53.08 |
| | Decrease in selectivity (%) | | −13.2 | −0.31 | −4.51 | −18.02 |
| | Decreasing rate of selectivity (%/h) | | −0.00184 | −4.31E−05 | −0.000629 | −0.002512 |
| | Decrease in selectivity per propane WHSV (% h) | | −9.6 | −0.224947 | −3.283348 | −13.10829 |
| Comparative Example C | Reaction time (h) 0 | 90.9 | 55.4 | 4.09 | 0.00 | 59.49 |
| | Reaction time (h) 3524 | 86.8 | 49.7 | 0.85 | 0.00 | 50.55 |
| | Decrease in selectivity (%) | | −5.7 | −3.24 | 0.00 | −8.94 |
| | Decreasing rate of selectivity | | −0.000794 | −0.000452 | 0 | −0.001246 |

TABLE 2-continued

Catalyst life tests

|  | Propane conversion | Acrylonitrile selectivity | Acrylic acid selectivity | Propylene selectivity | Total selectivity % |
|---|---|---|---|---|---|
| (%/h) Decrease in selectivity per propane WHSV (% h) |  | −31.31868 | −17.80151 | 0 | −49.12019 |

In Table 2, the decreasing rate of selectivity means the degree of the decrease in catalytic activities in the case where the catalyst was used for a long period of time, and the decrease in selectivity per propane space velocity WHSV, shows that the smaller the value, the better the degree of the activity maintenance of the catalyst to the load by supply of the propane starting material. They are values obtained as follows.

1) Decreasing rate of selectivity=(initial selectivity−final selectivity)/reaction time When this value is compared among Example A (A), Comparative Example B (B) and Comparative Example C (C), decreasing rate of acrylonitrile (AN) selectivity C<A<B (C is good)

decreasing rate of acrylic acid (AA) selectivity B<C<A (B is good)

decreasing rate of propylene (PPY) selectivity A<C<B (A is good)

decreasing rate of the total (AN+AA+PPY) selectivity A<B<C (A is good)

2) Decrease in selectivity per propane WHSV=(initial selectivity−final selectivity)/propane WHSV When this value is compared among Example A (A), Comparative Example B (B) and Comparative Example C (C), decreasing rate of acrylonitrile (AN) selectivity A<B<C (A is good)

decreasing rate of acrylic acid (AA) selectivity B<A<C (B is good)

decreasing rate of propylene (PPY) selectivity A<C<B (A is good)

decreasing rate of the total (AN+AA+PPY) selectivity A<B<C (A is good).

From the foregoing Example A and Comparative Examples B and C, it is evident that A is superior in most cases, and yet in the total selectivity, A is the best in every evaluation, and from the overall evaluation, A is superior. Accordingly, it is evident that the present invention is effective also for the maintenance of the catalytic activities.

INDUSTRIAL APPLICABILITY

According to the method of the present invention, in the ammoxidation reaction of propane, the reaction is carried out by selecting the molar ratio of propane to ammonia and the oxygen ratio, whereby acrylonitrile and acrylic acid can be produced at high selectivity and in high yield in the total amount. Further, the catalytic activities can be maintained over a long period of time, and the reaction can be carried out efficiently and constantly for a long period of time. As used herein, "JP-A" and "JP-B" refer to Japanese Unexamined Patent Publication and Japanese Examined Publication, respectively.

What is claimed is:

1. A method for the simultaneous production of acrylonitrile and acrylic acid by reacting propane with ammonia and oxygen in the gas phase catalytic oxidation in the presence of a metal oxide catalyst containing vanadium and at least one member selected from the group consisting of tellurium, antimony and molybdenum, and adjusting the molar ratio of propane to ammonia in the range of from 2 to 10 and the molar ratio of oxygen to ammonia in the range of from 2 to 10.

2. The method for simultaneous production of acrylonitrile and acrylic acid according to claim 1, wherein the metal oxide catalyst is selected from the group consisting of molybdenum, vanadium, and at least one of tellurium and antimony.

3. The method for simultaneous production of acrylonitrile and acrylic acid according to claim 1, wherein the metal oxide catalyst contains molybdenum, vanadium, X, Y and oxygen, wherein X is at least an element selected from the group consisting of tellurium and antimony, and Y is at least one element selected from the group consisting of niobium, tantalum, tungsten, titanium, aluminum, zirconium, chromium, manganese, iron, ruthenium, cobalt, rhodium, nickel, palladium, platinum, bismuth, boron, indium, phosphorus, a rare earth element, an alkali metal and an alkaline earth metal, and the proportions of the above respective components, except for oxygen, are represented by the following formulae:

$$0.25 < r\text{Mo} < 0.98$$

$$0.003 < r\text{V} < 0.5$$

$$0.003 < r\text{X} < 0.5$$

$$0.003 < r\text{Y} < 0.5.$$

4. The method for simultaneous production of acrylonitrile and acrylic acid according to claim 3, wherein Y contains at least niobium.

5. The method for simultaneous production of acrylonitrile and acrylic acid according to claim 3, wherein Y is selected from the group consisting of niobium and at least one of boron and cerium.

6. The method for simultaneous production of acrylonitrile and acrylic acid according to claim 1, wherein the molar ratio of propane to ammonia is from 2.5 to 10.

7. The method for simultaneous production of acrylonitrile and acrylic acid according to claim 1, wherein the ratio of oxygen to ammonia is from 3 to 8.

8. The method for simultaneous production of acrylonitrile and acrylic acid according to claim 1, wherein the reaction is carried out in a fluidized bed reactor.

9. The method for simultaneous production of acrylonitrile and acrylic acid according to claim 1, wherein the reaction is carried out in a fluidized bed reactor wherein the gas space velocity is from 100 to 10000/h, the space velocity based on mass of propane is from 0.05 to 6.0/h, the space velocity based on mass of oxygen is from 0.05 to 6.0/h, and the reaction temperature is from 340 to 480° C.

10. The method for simultaneous production of acrylonitrile and acrylic acid according to claim 1, wherein the reaction is carried out in a fluidized bed reactor wherein the gas space velocity is from 500 to 9000/h, the space velocity based on mass of propane is from 0.07 to 4.0/h, the space velocity based on mass of oxygen is from 0.2 to 4.5/h, and the reaction temperature is from 380 to 460° C.

11. The method for simultaneous production of acrylonitrile and acrylic acid according to claim 1, which contains a step wherein a gas containing acrylonitrile and acrylic acid, discharged from the reactor, is absorbed by a dilute sulfuric acid aqueous solution, and then acrylonitrile and acrylic acid are separated by a distillation operation.

12. The method for simultaneous production of acrylonitrile and acrylic acid according to claim 1, wherein the molar ratio of the formed acrylic acid to the formed acrylonitrile is adjusted to be from 0.01 to 5.0.

13. The method for simultaneous production of acrylonitrile and acrylic acid according to claim 1, wherein the molar ratio of the formed acrylic acid to the formed acrylonitrile is adjusted to be from 0.05 to 2.0.

* * * * *